United States Patent [19]

Eberhard et al.

[11] Patent Number: 5,073,910

[45] Date of Patent: Dec. 17, 1991

[54] SQUARE WAVE CONE BEAM SCANNING TRAJECTORY FOR DATA COMPLETENESS IN THREE-DIMENSIONAL COMPUTERIZED TOMOGRAPHY

[75] Inventors: Jeffrey W. Eberhard; Kristina H. V. Hedengren, both of Schenectady, N.Y.

[73] Assignee: General Electric Company, Schenectady, N.Y.

[21] Appl. No.: 572,651

[22] Filed: Aug. 27, 1990

[51] Int. Cl.⁵ ............................................. G01N 23/00
[52] U.S. Cl. ....................................... 378/4; 378/11; 378/22; 378/23; 378/901
[58] Field of Search ............ 378/4, 9, 10, 22, 901, 378/99, 11, 13, 17, 23

[56] References Cited

U.S. PATENT DOCUMENTS 4,752,691 6/1988 Hawman ............................... 378/10

OTHER PUBLICATIONS

"The Dynamic Spatial Reconstructor", R. A. Robb et al., J. Med. Syst., vol. 4, No. 2, pp. 253-288 (1980).
"Iterative Three-Dimensional Reconstruction from Twin-Cone Beam Projections", M. Schlindwein, IEEE Trans. Nucl. Sci., vol. NS-25, No. 5, pp. 1135-1143 (Oct. 1978).
"Convolutional Reconstruction from Cone-Beam Projection Data", G.N. Minerbo, IEEE Trans. Nucl. Sci., vol. NS-26, No. 2, pp. 2682-2684 (Apr. 1979).
"An Inversion Formula for Cone-Beam Reconstruction", H. K. Tuy, SIAM J. Math., vol. 43, No. 3, pp. 546-552 (Jun. 1983).
"Practical Cone-Beam Algorithm", L. A. Feldkamp et al., J. Opt. Soc. Am. A., vol. 1, No. 6, pp. 612-619 (Jun. 1984).
"Image Reconstruction from Cone-Beam Projections: Necessary and Sufficient Conditions and Reconstruction Methods", B. D. Smith, IEEE Trans. Med. Imag., vol. MI-44, pp. 14-25 (Mar. 1985).
"Quantitative Cone-Beam COnstruction", H. Hu et al., SPIE Medical Imaging III: Image Processing, vo. 1092, pp. 492-501 (1989).

Primary Examiner—Janice A. Howell
Assistant Examiner—Kim-Kwok Chu
Attorney, Agent, or Firm—Paul R. Webb, II; James C. Davis, Jr.

[57] ABSTRACT

A configuration for three-dimensional cone beam computerized tomography imaging which allows a complete data set to be acquired in a practical manner, while providing fast data acquisition to minimize motion artifacts. An object within a field of view such that every plane passing through the field of view passes through the source scanning trajectory at least once.

22 Claims, 10 Drawing Sheets

FIG. 1
PRIOR ART

FIG. 2c DETECTOR INTEGRALS
$\int X(\theta) d\theta = \iint f(r,\theta,z_0) dr d\theta$ FIG. 2f 3D CT IMAGE
$\hat{f}(x,y,z)$ FIG. 2b CONE BEAM DETECTOR DATA
$X(\theta) = \int f(r,\theta,z_0) dr$ FIG. 2e PARALLEL BEAM DETECTOR DATA
$\hat{X}(\theta) = \int f(x,y,z) ds$ FIG. 2a PART
$f(x,y,z)$ FIG. 2d RADON TRANSFORM
$\iint f(r,\theta,z_0) r dr d\theta$

SQUARE WAVE CONE BEAM SCANNING TRAJECTORY FOR DATA COMPLETENESS IN THREE-DIMENSIONAL COMPUTERIZED TOMOGRAPHY

BACKGROUND OF THE INVENTION

The present invention relates generally to three-dimensional (3D) computerized tomography (CT) and, more particularly, to methods and systems for acquiring a complete data set for reconstruction when cone beam geometry is employed.

In conventional computerized tomography for both medical and industrial applications, an x-ray fan beam and a linear array detector are employed. Two-dimensional (2D) imaging is achieved. While the data set is complete and image quality is correspondingly high, only a single slice of an object is imaged at a time. When a 3D image is required, a "stack of slices" approach is employed. Acquiring a 3D data set one 2D slice at a time is inherently slow. Moreover, in medical applications, motion artifacts occur because adjacent slices are not imaged simultaneously. Also, dose utilization is less than optimal, because the distance between slices is typically less than the x-ray collimator aperture, resulting in double exposure to many parts of the body.

One approach to acquiring a 3D data set simultaneously is described in the literature: Richard A. Robb, Arnold H. Lent, Barry K. Gilbert, and Aloysius Chu, "The Dynamic Spatial Reconstructor", J. Med. Syst., vol. 4, No. 2, pp. 253–288 (1980). The Dynamic Spatial Reconstructor employs twenty-eight x-ray sources and twenty-eight x-ray imaging systems in a synchronous scanning system to acquire data for a conventional "stack of slices" reconstruction all at once. The actual geometry is a stack of twenty-eight cone beams scanning twenty-eight respective cylindrical volumes, with area detectors employed to acquire 240 adjacent video lines of data for each slice. However, the data is analyzed as though it is from a stack of fan beam projections, stacked in an axial direction, using conventional 2D reconstruction algorithms. Consistent with this approach, in the Dynamic Spatial Reconstructor the divergence of the x-ray beam above and below the central slice of each cylindrical volume is only ±4.

In a system employing true cone beam geometry, a cone beam x-ray source and a 2D area detector are employed. An object is scanned, preferably over a 360 angular range, either by moving the x-ray source in a scanning circle around the object, while keeping the 2D area detector fixed with reference to the source, or by rotating the object while the source and detector remain stationary. In either case, it is relative movement between the source and object which effects scanning. Compared to the conventional 2D "stack of slices" approach to achieve 3D imaging, the cone beam geometry has the potential to achieve rapid 3D imaging of both medical and industrial objects, with improved dose utilization.

The cone beam geometry for 3D imaging has been discussed extensively in the literature, as represented by the following: M. Schlindwein, "Interactive three-Dimensional Reconstruction from Twin-Cone Beam Projections", IEEE Trans. Nucl.Sci., Vol. NS-25, No. 5, pp. 1135–1143 (October, 1978); Gerald N. Minerbo, "Convolutional Reconstruction from Cone-Beam Projection Data", IEEE Trans. Nucl. Sci., Vol. NS-26, No. 2, pp. 2682–2684 (April, 1979); Heang K. Tuy, "An Inversion Formula for Cone-Beam Reconstruction", SIAM J. Math., Vol. 43, No. 3, pp. 546–552 (June, 1983); L. A. Feldkamp, L. C. Davis, and J. W. Kress, "Practical Cone-Beam Algorithm", J. Opt. Soc. Am. A., Vol. 1, No. 6, pp. 612–619 (June, 1984); Bruce D. Smith, "Image Reconstruction from Cone-Beam Projections: Necessary and Sufficient Conditions and Reconstruction Methods", IEEE Trans. Med. Imag., Vol. MI-44, pp. 14–25 (March, 1985); and Hui Hu, Robert A. Kruger, and Grant T. Gullberg, "Quantitative Cone-Beam Construction", SPIE Medical Imaging III: Image Processing, Vol. 1092, pp. 492–501 (1989).

Figure 1:
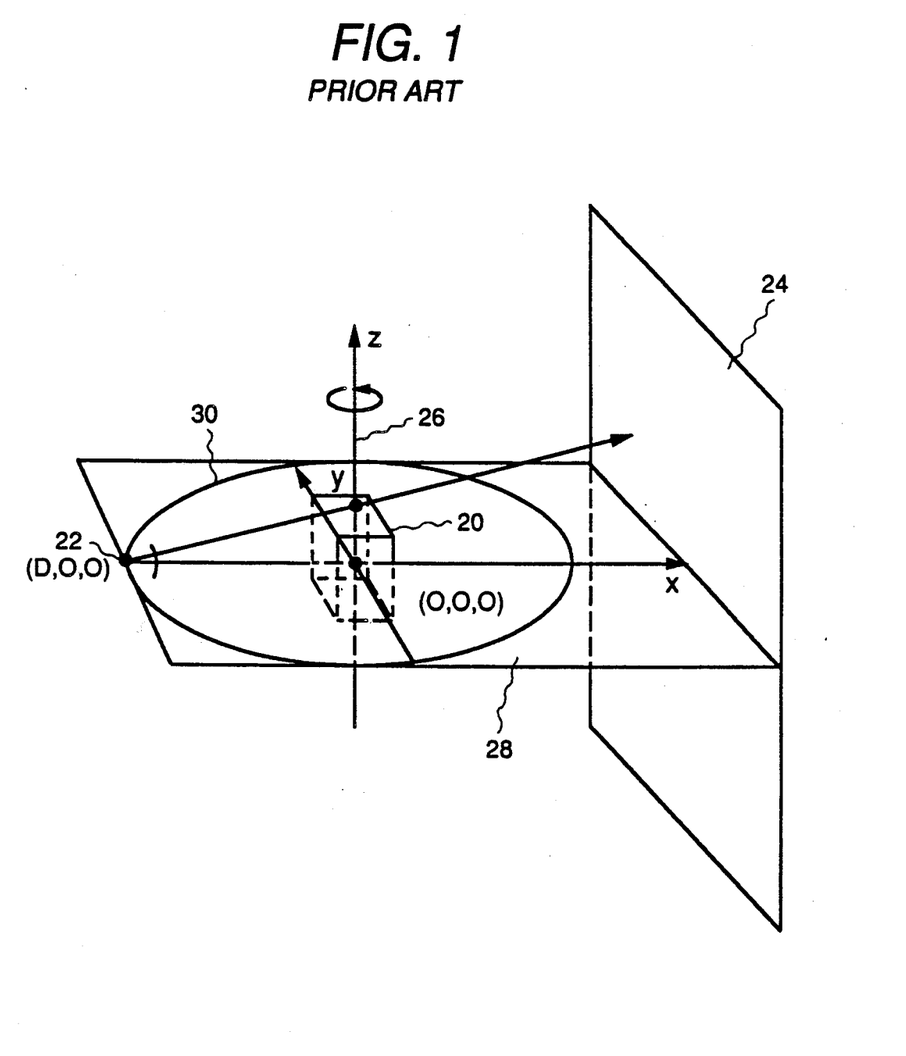
FIG. 1, referred to hereinabove, represents conventional cone beam scanning geometry for 3D CT.

A typical scanning and data acquisition configuration employing cone-beam geometry is depicted in FIG. 1. An object 20 is positioned within a field of view between a cone beam x-ray point source 22 and a 2D detector array 24, which provides cone beam projection data. An axis of rotation 26 passes through the field of view and object 20. For purposes of analysis, a midplane 28 is defined which contains the x-ray point source 22 and is perpendicular to the axis of rotation 26. By convention, the axis of rotation 26 is referred to as the z-axis, and the intersection of the axis of rotation 26 and the midplane 28 is taken as the origin of coordinates. x and y axes lie in the midplane 28 as indicated, and the (x,y,z) coordinate system rotates with the source 22 and detector 24. For scanning the object 20 at a plurality of angular positions, the source 22 moves relative to the object 20 and the field of view along a circular scanning trajectory 30 lying in the midplane 28, while the detector 24 remains fixed with respect to the source 22.

Thus, in the configuration of FIG. 1, data are acquired at a number of angular positions around the object by scanning the source and detector along the single circular scanning trajectory 30 (or equivalently rotating the object while the source and detector remain stationary). However, as demonstrated in the literature (e.g. Smith, 1985, above), and as described in greater detail hereinbelow, the data set collected in such a single scan is incomplete. In typical systems, the fraction of missing data can range from 1% to 5% or more, with non-uniform missing data distribution. Missing data introduces artifacts during image reconstruction, resulting in images which can be inadequate for medical diagnosis or part quality determination purposes.

Smith, 1985, above has shown that a cone beam data set is complete if there is a point from the x-ray source scanning trajectory on each plane passing through the object of interest (with the assumptions that the detector is locked in position relative to the source and large enough to span the object under inspection). A configuration suggested by Minerbo (1979, above) and Tuy (1983, above), which Smith points out satisfies his condition for data completeness, is to employ two circular source scanning trajectories which are perpendicular to each other. Such a scanning configuration is however difficult to implement as a practical matter.

Thus, previous cone beam data acquisition and imaging configurations either provide incomplete data (e.g. single circular source scanning trajectory) or provide complete data in configuration which is complex, difficult or impractical to implement (two perpendicular source scanning trajectories).

SUMMARY OF THE INVENTION

Accordingly, it is an object of the invention to provide a configuration for cone beam 3D CT imaging which provides a complete data set.

It is another object of the invention to provide such a configuration for cone beam 3D CT imaging which may be readily implemented as a practical matter, with minimal complexity.

Briefly, and in accordance with an overall aspect of the invention, it is recognized that a square wave source scanning trajectory can satisfy Smith's criterion for data completeness in 3D CT imaging, and can readily be implemented as a practical matter.

Thus, in accordance with one aspect of the invention a scanning and data acquisition method for three-dimensional computerized tomography (CT) imaging of an object within a field of view includes the steps of defining a source scanning trajectory as a square wave on a cylindrical surface surrounding the field of view such that every plane passing through the field of view passes through the source scanning trajectory at least once. A cone beam x-ray source and a two-dimensional array detector positioned with reference to the source and with reference to the field of view are employed to scan the object at a plurality of points along the source scanning trajectory to obtain cone beam projection data.

In accordance with another aspect of the invention, a scanning and data acquisition system for three-dimensional computerized tomography imaging of an object within a field of view includes a cone beam x-ray source and a two-dimensional array detector positioned with reference to the source and the field of view for obtaining cone beam projection data. The system also includes a scanning element for effecting relative motion between the source and the object. The source moves relative to the object along a source scanning trajectory defined as a square wave on a cylindrical surface surrounding the field of view such that every plane passing through the field of view passes through the scanning trajectory at least once. Thus, cone beam projection data is acquired with the source at a plurality of points on the scanning trajectory.

The scanning element may comprise a two-axis CNC part manipulator connected to the object for translating and rotating the object while the source and detector remain stationary. Alternatively, the scanning element may comprise a two-axis CNC part manipulator connected to the source and detector for translating and rotating the source and detector about the object while the object remains stationary.

In either the method or the system of the invention, source scanning trajectories with any number of square wave cycles may be employed. For example, the trajectory may be defined as an even number, such as two cycles of a square wave on a cylinder. As another example, the trajectory may be defined as any odd number, such as three, cycles of a square wave on the cylindrical surface. These provide even and odd symmetry data sets, respectively, which are expected to have different orthogonality and redundancy properties in reconstruction.

In accordance with the invention, the source may be moved along the scanning trajectory in either a continuous or a step-wise scan.

As stated above, the basic criterion for the square wave source scanning trajectory is that every plane passing through the field of view passes through the scanning trajectory at least once. Defined below, in terms of dimensional relationship, are two scanning trajectories in particular which meet this criterion have been developed.

In particular, for a cylindrical field of view having a radius no greater than $r_o$ and length no greater than $\pm A_o$, a two-cycle symmetrical square wave scanning trajectory may be defined as $$x(\theta) = r_p \cos \theta$$

$$y(\theta) = r_p \sin \theta$$

$$z(\theta) = \begin{cases} +A_p \text{ for } 0 < \theta < \frac{\pi}{2} \text{ and } \pi < \theta < \frac{3\pi}{2} \\ -A_p \text{ for } \frac{\pi}{2} < \theta < \pi \text{ and } \frac{3\pi}{2} < \theta < 2\pi, \\ Z \text{ where } -A_p \leq Z \leq A_p \text{ for } \theta = 0, \frac{\pi}{2}, \pi, \frac{3\pi}{2} \end{cases}$$

where $r_p$ is the radius of the scanning trajectory and $A_p$ is the amplitude of the scanning trajectory. Defining $$\alpha = \frac{r_p}{r_0} \text{ and } \beta = \frac{A_p}{A_0},$$

either of the following two sets of conditions result in a complete data set:

$$\alpha = \sqrt{2}, \text{ and } \beta = 1, \text{ or } \alpha = \beta = 1.34.$$

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION

Since the present invention is directed to providing a complete data set for 3D CT when a cone beam scanning geometry is employed, what is meant by data set completeness will next be defined and described, followed by a description of methods and systems in accordance with the invention.

Figure 2A:
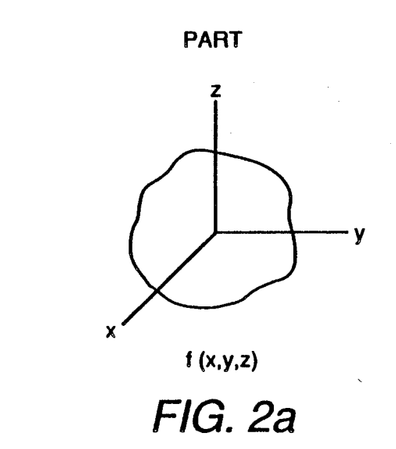
FIGS. 2a, 2b, 2c, 2d, 2e and 2f are diagrams depicting the Radon transform approach to 3D CT imaging.
Figure 2B:
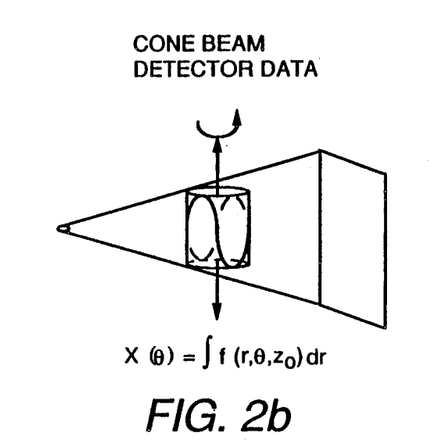
Figure 2C:
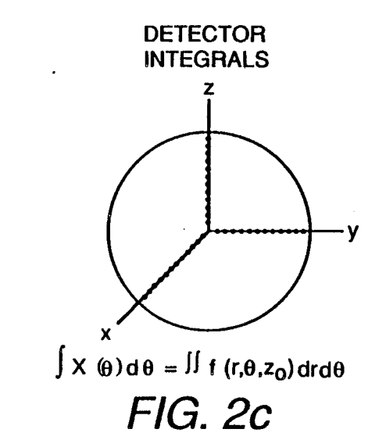
Figure 2D:
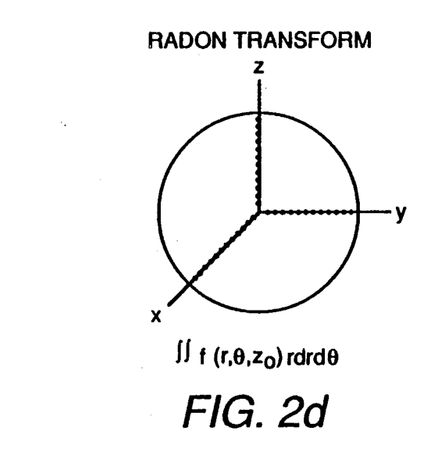
Figure 2E:
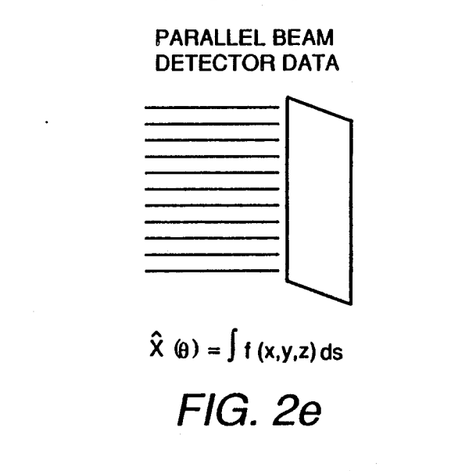
Figure 2F:
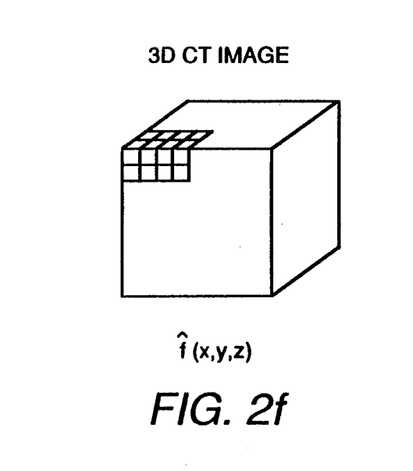

Data set completeness can be defined most clearly and rigorously in terms of the Radon transform approach to 3D imaging, represented in FIGS. 2a through 2f. The object itself is defined in terms of its x-ray attenuation coefficient f(x,y,z) (FIG. 2a). The measured cone beam projection data then corresponds to a line integral of this function over the radial direction $X(\theta) = \int (r,\theta,z_o)dr$ (FIG. 2b). The line integrals of the detector data (also known as detector integrals) are given by $\int X(\theta)d\theta = \int\int f(r,\theta,z_o)dr\, d\theta$ (FIG. 2c). In the parallel beam case, these detector integrals are simply equal to the Radon transform of the object. In the cone beam case, however, the Radon transform is given instead by $\int\int f(r,\theta,z_o)r\, dr\, d\theta$ (FIG. 2d). The additional factor of r in the Radon transform integral results from the Jacobian of the coordinate transformation from Cartesian to polar coordinates. As depicted in FIGS. 2e and 2f, an inverse Radon transform procedure reconstructs a 3D CT image from the detector integrals. Since direct inverse Radon transformation requires planar integrals of the object as input, an intermediate step of converting cone beam detector integrals to planar integrals may be employed, although a variety of reconstruction techniques are available, as is apparent from the literature.

It is significant to note that the data set is complete if it provides data at every point in Radon transform space; i.e., Radon space is filled with data over the region of support corresponding to the field of view in real space within which the object of interest fits. Therefore, the filling of Radon space by various scanning configurations is of significant interest. (In addition, it can be shown that if detector integral space is filled over the region of support for the object, the data set is complete.)

Figure 3:
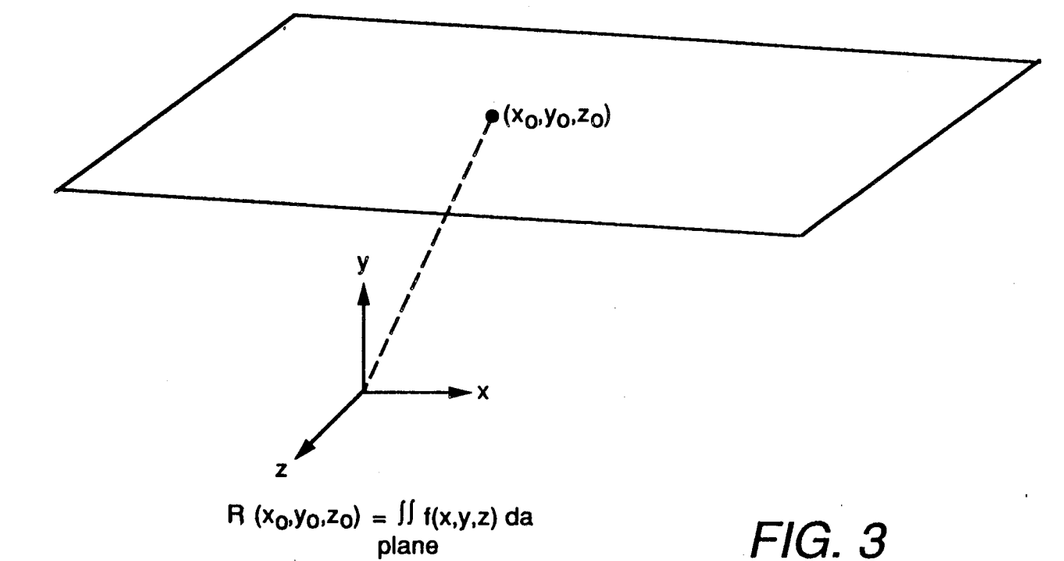
FIG. 3 is a representation of the 3D Radon transform of an object at a given point.

As depicted in FIG. 3, the Radon transform of an object at a point $x_0, y_0, z_0$ is given by the area integral of the x-ray attenuation coefficient over the plane passing through $x_0, y_0, z_0$ that is perpendicular to the line from the origin to $x_0, y_0, z_0$, and can be expressed as $$R(x_0, y_0, z_0) = \iint_{\text{plane}} f(x,y,z) da$$

In 2D, the situation is similar, except that the integral is over a line, not over a plane.

Any scanning and data acquisition configuration provides data over some volume of Radon space. Described next with reference to FIGS. 4a through 7b are regions in Radon space which are filled and which are not for various 2D and 3D scanning configurations.

Figure 4A:
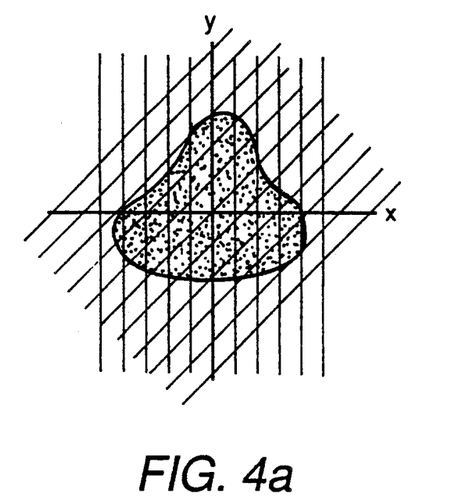
FIGS. 4a and 4b depict Radon space filling in the case of 2D parallel beam CT.
Figure 4B:
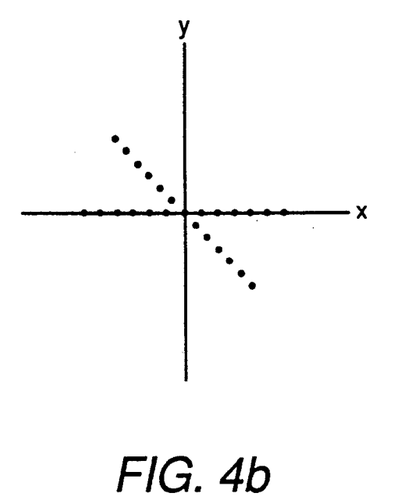
Figure 5A:
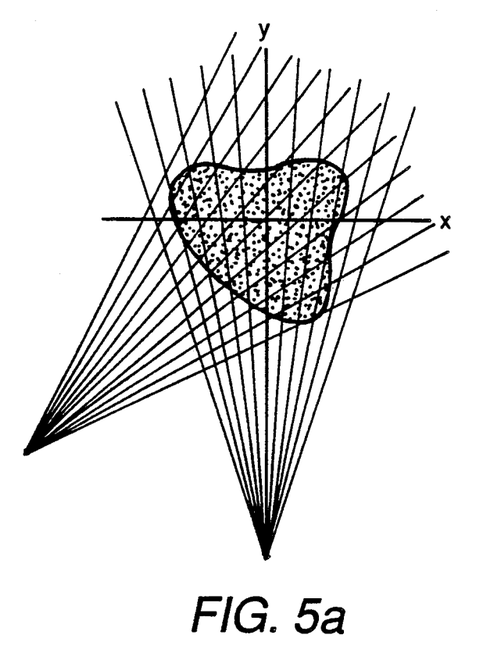
FIGS. 5a and 5b depict Radon space filling in the case of 2D fan beam CT.
Figure 5B:
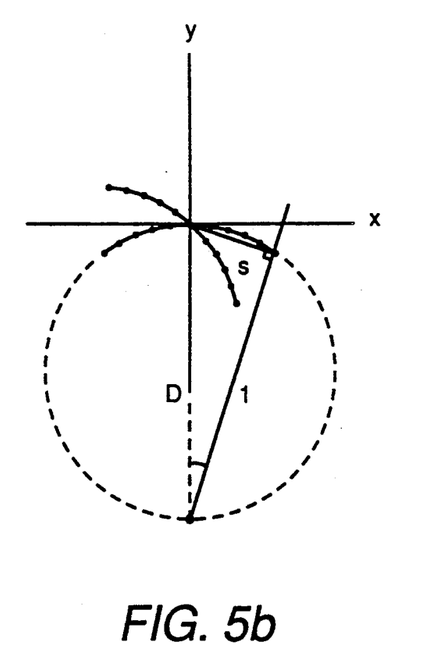

FIGS. 4a and 4b represent Radon space filling for 2D parallel beam CT. The x-ray paths for two view angles are shown in FIG. 4a, and the resulting points in Radon space are shown in FIG. 4b. For each point in Radon space, a line is extended from the origin to the point of interest, and the x-ray intensity is integrated over a line passing through that point and perpendicular to the line to that point from the origin. Such points are shown in FIG. 4b for each ray depicted in FIG. 4a, for each of two view angles.

The situation for fan beam data acquisition is similar (FIGS. 5a and 5b), but here the ray paths diverge from the x-ray source, and the geometry is slightly more complicated. The procedure is the same, however. By way of example, the extreme right-hand ray of the fan beam is analyzed in FIG. 5b. The perpendicular line to the ray is labeled "s". It may be noted that the point of Radon space of interest forms a right triangle with the origin and the x-ray source point. (It is the same point that would be determined in parallel beam geometry for a view angle orientation of one-half the fan angle.) This is generally true for any point in Radon space acquired with the detector in this position. Therefore, by geometry, the points in Radon space lie on the arc of a circle whose diameter is the source to center of rotation distance. Similar arcs are constructed for each view angle position around the object. It can be appreciated from this construct that complete data is provided by rotating source and detector around the object through an angle of 180° plus the fan angle.

Figure 6A:
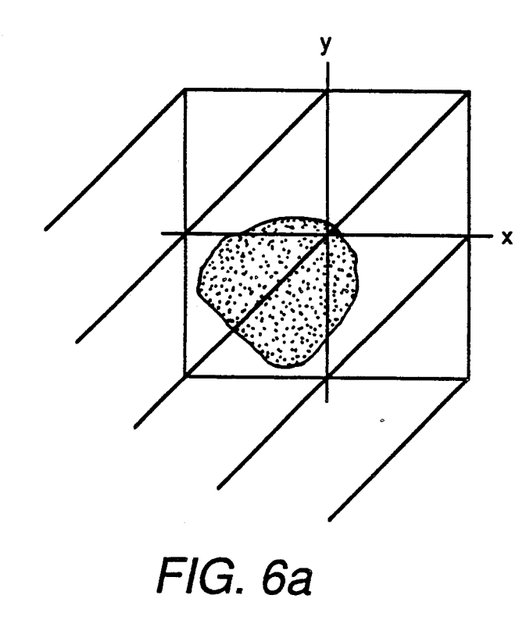
FIGS. 6a and 6b depict Radon space filling in the case of 3D parallel beam CT.
Figure 6B:
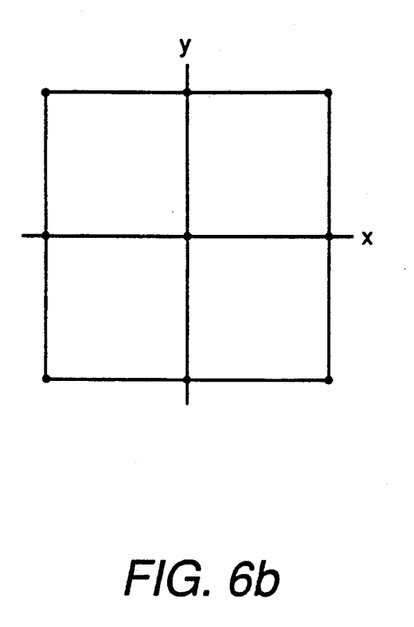

The parallel beam case for 3D is represented in FIGS. 6a and 6b. Here, the x-ray attenuation measurement corresponds to integration in the z direction, and line integrals of the detector data are taken at other orientations in the detector plane to fill in Radon space on a single plane passing through the object. For example, the point in Radon space at $x=0$, $y=y_o$ corresponds to the detector integral over points in the detector a distance $y_o$ above the x,z plane. Points off axis in Radon space correspond to detector integrals along straight lines with various slopes in detector space. For example, the point at $x=c$, $y=c$ in Radon space corresponds to detector integrals along lines with slop $-45°$ with respect to the x axis and a distance $\sqrt{2}c$ from the origin.

Figure 7A:
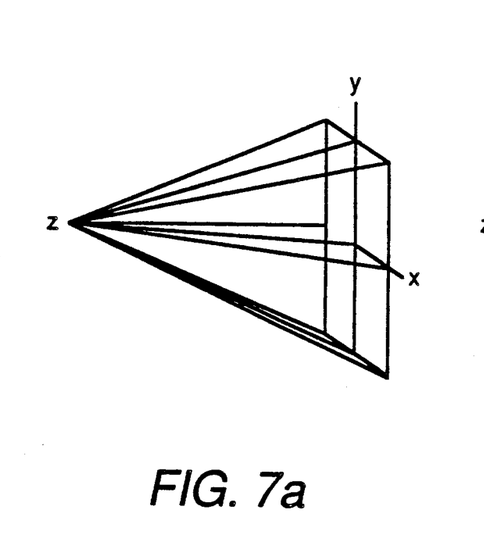
FIGS. 7a and 7b depict Radon space filling in the case of 3D cone beam CT.
Figure 7B:
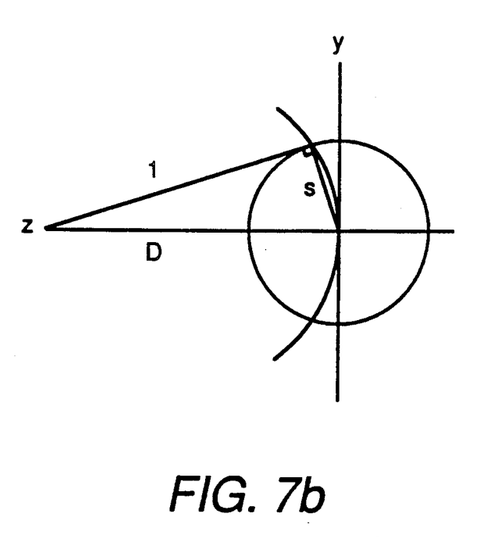
Figure 8:
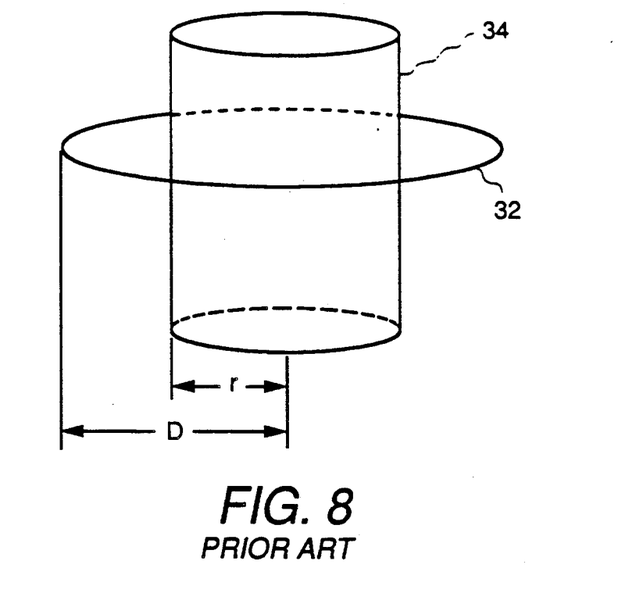
FIG. 8 depicts a prior art circular scanning trajectory corresponding to FIG. 1.
Figure 9:
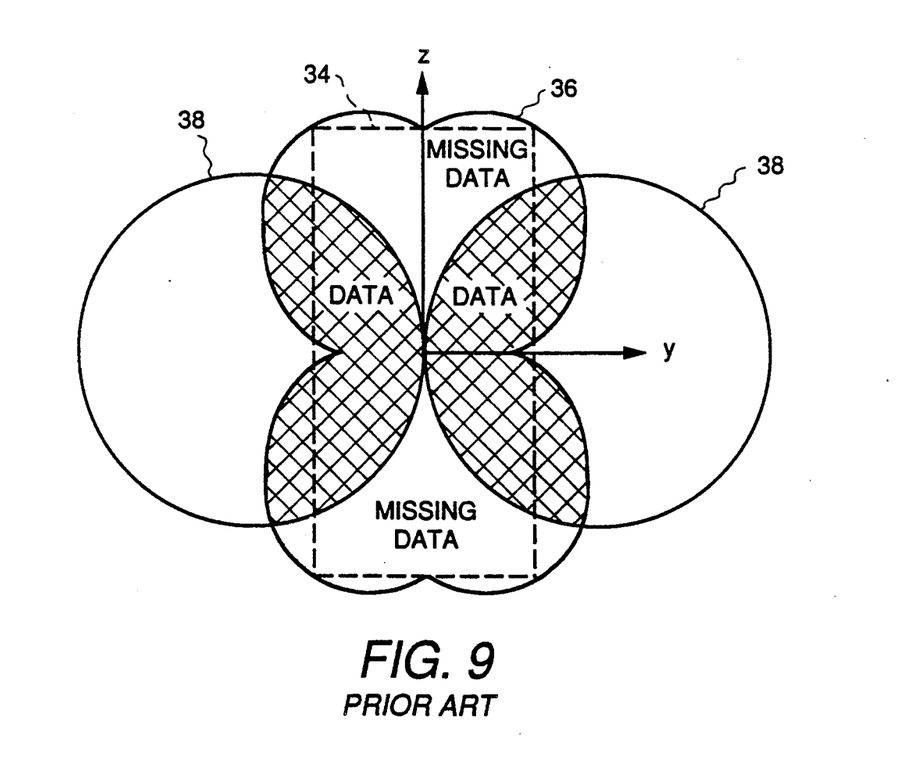
FIG. 9 depicts regions of available data and missing data in Radon space when the prior art scanning configuration of FIGS. 1 and 8 is employed.

The particularly relevant cone beam case in 3D is similarly represented in FIGS. 7a and 7b. Corresponding to FIGS. 7a and 7b are prior art FIG. 1, described hereinabove; prior art FIG. 8, which depicts a single circular source scanning trajectory 32 around a cylindrical field of view 34 of radius $r_o$ within which an object to be scanned fits; and prior art FIG. 9, which depicts in cross-section the intersection of a volume 36 in Radon space comprising the region of support for the cylindrical field of view 34 with a toric volume 38 representing the region in Radon space for which data are available. In FIG. 9, the diameter of each side of the toric volume 38 is equal to the source to axis of rotation distance D. For purposes of comparison with the Radon space region of support volume 36, superimposed in phantom in FIG. 9 is the real space field of view 34.

In FIGS. 7a and 7b, the exemplary point shown in Radon space corresponds to the detector integral along the top line of the detector data. The geometry is similar to the fan beam case in 2D. The points in Radon space for all detector line integrals at a single view angle correspond to a section of a sphere with diameter equal to the source to center of rotation distance. A new spherical shell of data is created at each view angle, and for a 360° scan, the available data falls inside the toric volume 38 (FIG. 9).

Thus, as represented in FIG. 9, in Radon space data for reconstruction are available at those points within the region of support volume 36 where the region of support volume 36 intersects the toric volume 38, as indicated by the word "data". As indicated by the words "missing data", data are absent for points on the top and bottom of the region of support volume 36 in Radon space because these points correspond to planes parallel and near parallel to the x,y plane and data for these planes are not available because of the cone beam nature of the x-ray source. The region of missing data narrows as z approaches the midplane, and for z=0 (on the midplane), all the required data are available.

As shown by Smith, 1985, above, a cone beam data set is complete if there is a point from the x-ray source scanning trajectory on each plane passing through the object of interest. (The detector is assumed to be locked in position relative to the source and large enough to span the object under inspection.) Relating this to FIG. 8 where the circular source scanning trajectory 32 surrounds the exemplary field of view 34, by Smith's criterion the trajectory 32 is incomplete because a number of horizontal and near-horizontal planes pass through the region of support of the object (i.e. the field of view 34) without intersecting the source scanning trajectory 32. These planes are exactly those that correspond to the missing data in Radon space in FIG. 9. When applying Smith's criterion, it may be noted that, for large z, the number of planes through the object not intersecting the source scanning trajectory is relatively large, and the number decreases as z decreases. This same behavior is noted in Radon space, as shown in FIG. 9. It may also be noted that vertical planes passing through the object do intersect the scanning trajectory, and that, as the diameter of the trajectory increases relative to the diameter of the object, the amount of missing data (the number of planes that do not intersect the scanning trajectory) decreases.

Figure 10:
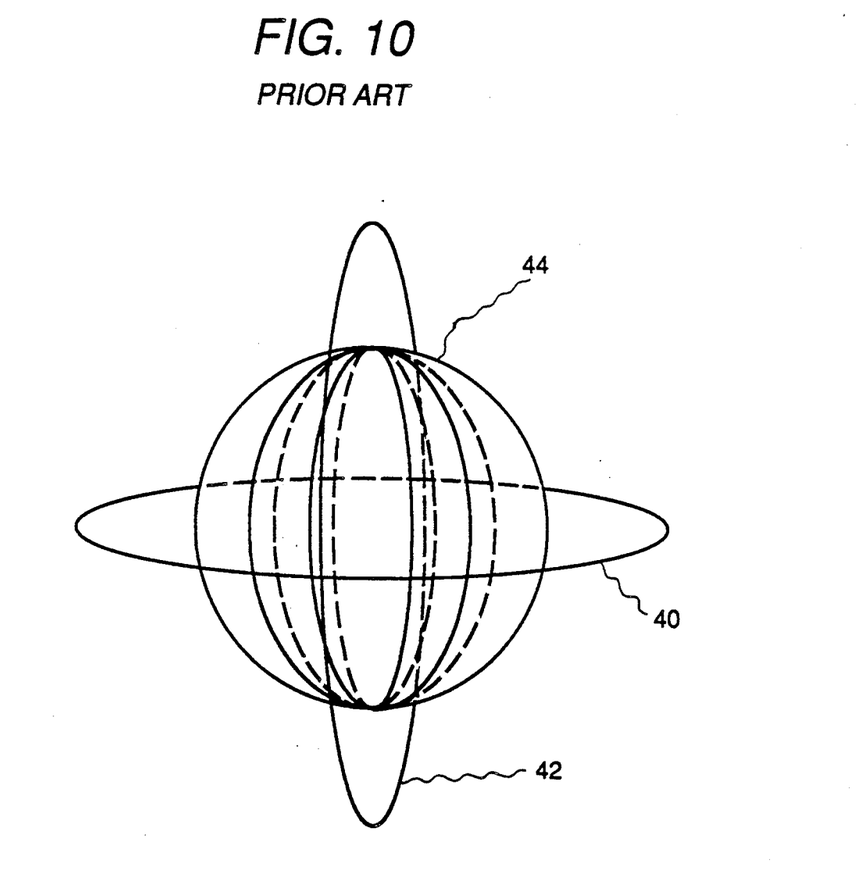
FIG. 10 depicts a prior art dual perpendicular source scanning trajectory configuration.

As noted above, Minerbo (1979) and Tuy (1983) have suggested a dual perpendicular source circle scanning trajectory, as is represented in prior art FIG. 10 by two perpendicular circles 40 and 42 around an exemplary spherical field of view 44. For objects that fit inside this trajectory, complete data is available. However, for many industrial applications, the dual perpendicular scanning trajectory is difficult to implement because it requires complex fixturing or re-gripping of the part during the scan.

In accordance with the invention, a square wave scanning trajectory provides a complete data set for reconstruction, and may readily be implemented as a practical matter.

Figure 11:
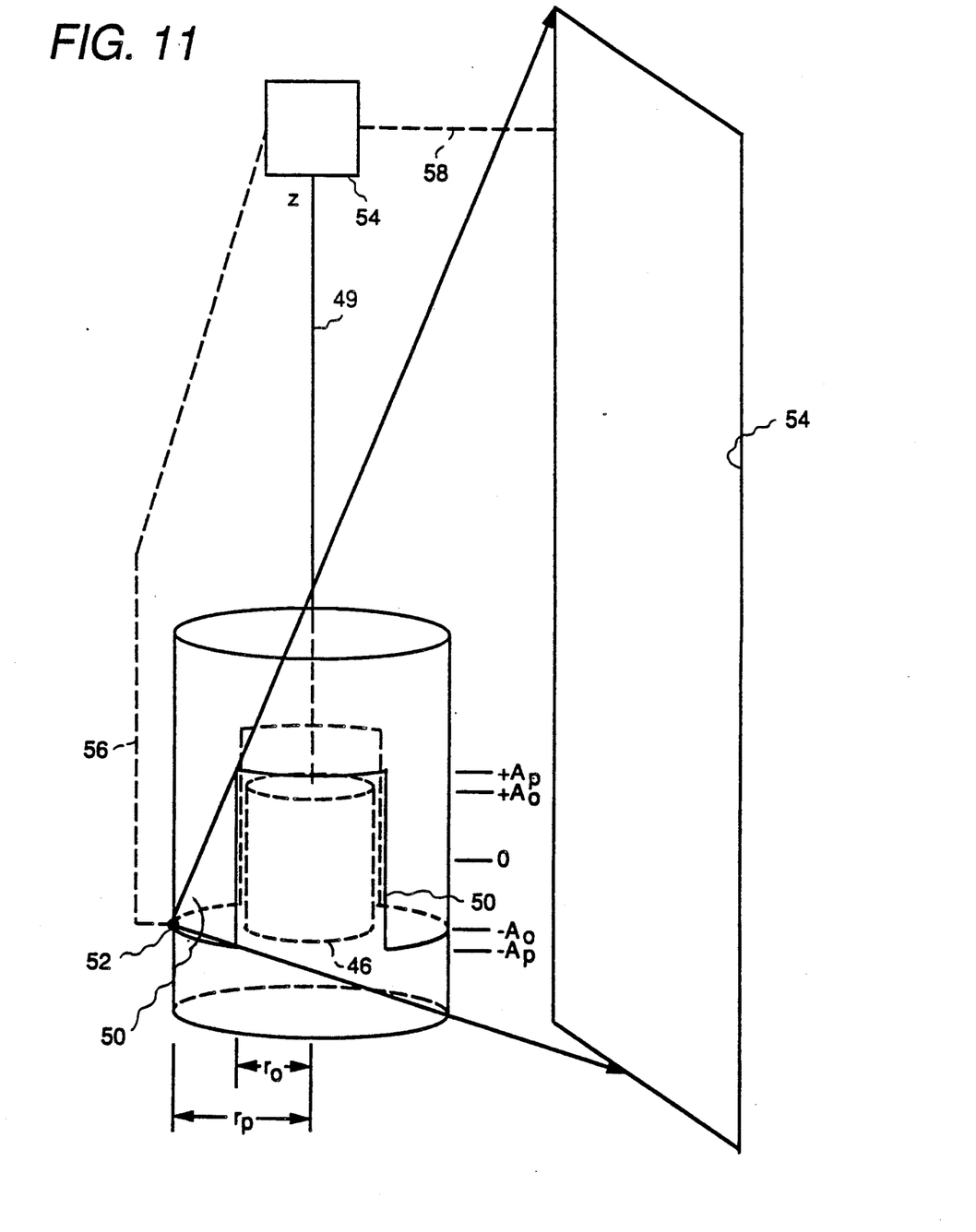
FIG. 11 depicts a square wave scanning trajectory in accordance with the invention.

With reference to FIG. 11, a cylindrical field of view 46 contains an object (not shown) or a portion of an object which is desired to be imaged. The field of view 46 is centered on a z-axis or axis of rotation 49 and has a length or axial extent along the z-axis ranging from $+A_0$ to $-A_0$. With reference to the top view of FIG. 12, the field of view 46 has a radius $r_0$. The particular coordinate system employed is represented in FIG. 13, from which it will be appreciated that every point within the coordinate system can be represented by two coordinates, z and $\theta$.

Figure 12:
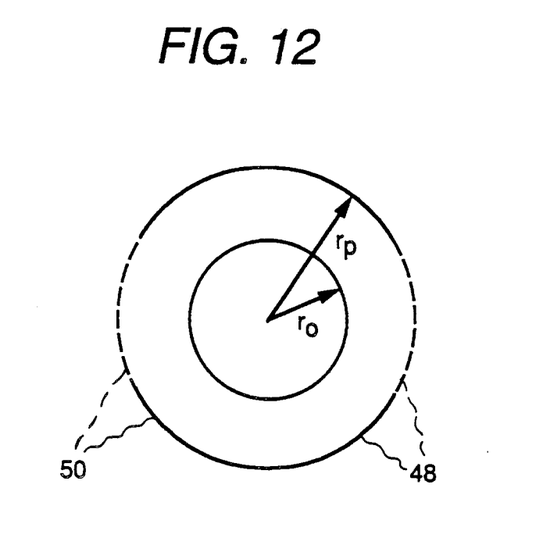
FIG. 12 is a top view of the geometry depicted in FIG. 11.
Figure 13:
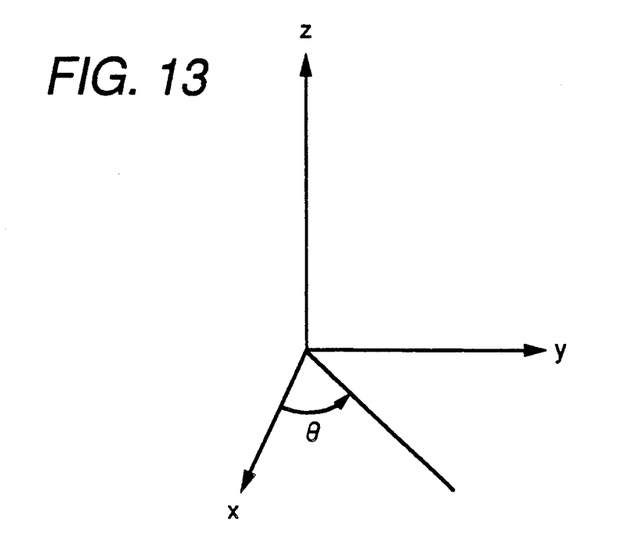
FIG. 13 further represents the coordinate system employed in FIGS. 11 and 12.

Also visible in FIGS. 11 and 12 is a cylindrical surface 48 used to define the radial position of a square wave source scanning trajectory 50. The radius of the cylindrical surface 48 and thus of the scanning trajectory 52 is defined as $r_p$.

In the particular embodiment of FIG. 11, the scanning trajectory 50 is defined as two complete square wave cycles on the cylindrical surface 48. The amplitude or height of the scanning trajectory 50 is defined as $\pm A_p$. With appropriate sizing of the scanning trajectory 50 relative to the field of view 46, Smith's condition can be satisfied, namely, that every plane passing through the field of view 46 passes through the scanning trajectory 50 at least once.

Depicted in FIG. 11 are a cone beam x-ray source 52 at a point along the source scanning trajectory 50, and a two-dimensional array detector 54 positioned with reference to the source 52 and with reference to the field of view 46 so as to scan the object (not shown) within the field of view 46 at a plurality of points along the source scanning trajectory 50 to obtain cone beam projection data. The detector 54 is locked in position 54 relative to the source 52, and large enough to span the field of view 46.

For effecting relative motion between the source 52 and object within the field of view 46 (with the source 52 moving along the source scanning trajectory 50), a scanning element 54 is provided. In FIG. 11, the scanning element 54 is shown in generalized form, and typically comprises a two-axis CNC part manipulator, the two axes being a vertical translation axis and a rotation axis. As a first alternative, the scanning element 54 can be connected to the object by a connection along the axis 49 in order to translate and rotate the object while the source 52 and detector 54 remain stationary. As a second alternative, the scanning element 54 can be connected to the source 52 and detector 54 by connections 56 and 58 shown in phantom for translating and rotating the source 52 and detector 54 together about the object while the object remains stationary. This second alternative is particularly applicable to medical applications.

Figure 14:
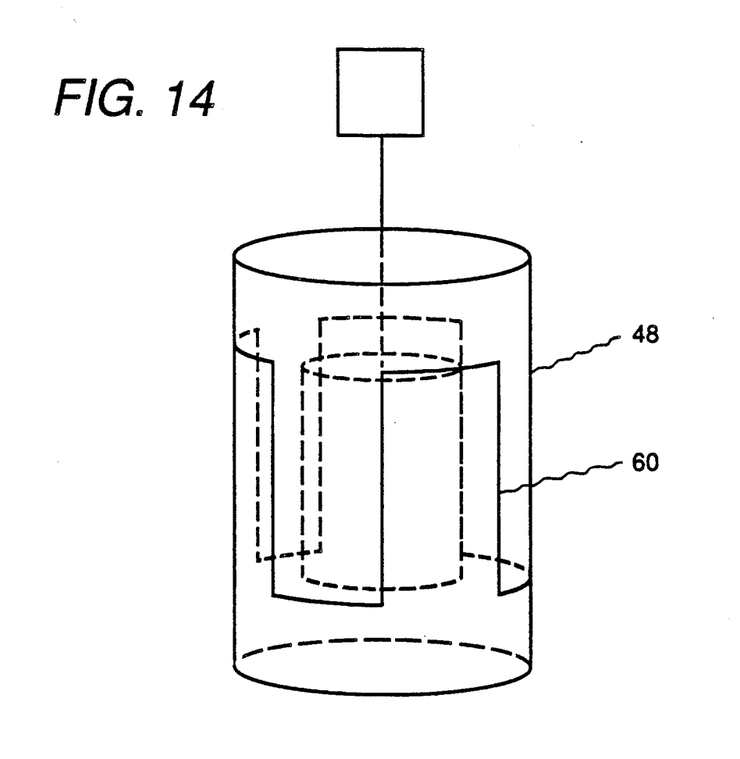
FIG. 14 depicts an odd symmetry square wave scanning trajectory in accordance with the invention.

FIG. 14 represents another source scanning trajectory 60, with three cycles of a square wave on the cylindrical surface 48. This scanning trajectory likewise provides a complete data set. However, at opposite sides of the cylinder, the source position is 180 out of phase in its scan cycle, to achieve odd symmetry, in contrast to the even symmetry of FIG. 11.

While both the even and odd symmetry data sets are complete, the even and odd symmetry data sets are expected to have different orthogonality and redundancy properties in reconstruction. Any combination of odd and even symmetry and any number of cycles may be used in a given scan to provide optimum system performance. Moreover, it will be appreciated that the scanning sequence need not be in the order indicated in the figures, since data are acquired at a set of discrete points along the trajectory in either event. Thus, scanning can be either step-wise or continuous as preferred.

Data acquisition time at each point can be adjusted to provide optimum data (e.g. best signal-to-noise ratio) over the entire scan. Spacing between data points can be adjusted to provide optimum data over the entire scanning trajectory or to provide advantages (e.g. complexity reduction or computational efficiency) depending on the particular image reconstruction algorithm employed. Scan speeds can be adjusted in continuous scanning mode to achieve advantages in data acquisition time or data point spacing.

While a variety of particular scanning trajectories may be employed which satisfies Smith's criterion, two in particular are defined here.

As defined hereinabove with reference to FIGS. 11, 12 and 13, a cylindrical field of view is defined having a radius no greater than $r_o$ and a length or longitudinal extent no greater than $\pm A_0$. For the two cycle, even symmetry case, the scanning trajectory may be defined as:

$$x(\theta) = r_p \cos \theta$$

$$y(\theta) = r_p \sin \theta$$

$$z(\theta) = \begin{cases} +A_p \text{ for } 0 < \theta < \frac{\pi}{2} \text{ and } \pi < \theta < \frac{3\pi}{2} \\ -A_p \text{ for } \frac{\pi}{2} < \theta < \pi \text{ and } \frac{3\pi}{2} < \theta < 2\pi, \\ Z \text{ where } -A_p \leq Z \leq A_p \text{ for } \theta = 0, \frac{\pi}{2}, \pi, \frac{3\pi}{2} \end{cases}$$

For convenience, two factors are defined, $$\alpha = \frac{r_p}{r_0} \text{ and } \beta = \frac{A_p}{A_0}.$$

In a case where the amplitude or height $A_P$ of the FIG. 11 source scanning trajectory 50 exactly corresponds with the height or amplitude $A_o$ of the field of view 46, the condition of data completeness is satisfied when $\alpha = \sqrt{2}$. In other words, the radius $r_p$ of the scanning trajectory is greater than the radius $r_o$ of the field of view, in particular $r_p = r_o\sqrt{2}$. Since in this case by definition $A_p = A_o$, then $\beta = 1$.

Another case where the data set is complete is where $\alpha = \beta = 1.34$. In this case, the radius $r_p$ of the source scanning trajectory 50 is greater than the $r_o$ of the field of view 46 by the factor 1.34, and the amplitude $A_p$ of the source scanning trajectory 50 is greater than the amplitude or height $A_0$ of the field of view 46 by the same factor 1.34.

It will be appreciated that, by geometry, a variety of other particular cases may be defined where Smith's criterion is satisfied for data completeness when a square wave scanning cycle is employed. It will further be appreciated that, while the present invention is described in the context of a cylindrical field of view, other field of view shapes may equally well be employed and analyzed, such as a spherical field of view.

The invention is also useful for medical imaging and for imaging large industrial parts where the object is larger than the actual field of view. While the resulting data set is somewhat incomplete, more data is provided than in the case of a single circular scanning trajectory.

While specific embodiments of the invention have been illustrated and described herein, it is realized that modifications and changes will occur to those skilled in the art. It is therefore to be understood that the appended claims are intended to cover all such modifications and changes as fall within the true spirit and scope of the invention.

What is claimed is:

1. A scanning and data acquisition method for three-dimensional computerized tomography (CT) imaging of a field of view containing at least a portion of an object illuminated by a cone beam source, said method comprising:

defining a source scanning trajectory as a path traversed by said source;

employing the cone beam source fixed with reference to a two-dimensional array detector with both source and detector movably positioned relative to the object in order to scan about the object;

specifying the source scanning trajectory as a square wave on a cylindrical surface surrounding the field of view such that each plane passing through the field of view intersects the scanning trajectory in at least one point; and scanning at a plurality of positions along the source scanning trajectory to obtain cone beam projection data.

2. A method in accordance with claim 1, which comprises specifying the source scanning trajectory as any even number of square wave cycles on the cylindrical surface.

3. A method in accordance with claim 2, which comprises specifying the source scanning trajectory as two complete square wave cycles on the cylindrical surface.

4. A method in accordance with claim 1, which comprises specifying the source scanning trajectory as any odd number of square wave cycles on the cylindrical surface.

5. A method in accordance with claim 4, which comprises specifying the source scanning trajectory as three complete square wave cycles on the cylindrical surface.

6. A method in accordance with claim 1, which comprises moving the source along the scanning trajectory in a continuous scan.

7. A method in accordance with claim 1, which comprises moving the source along the scanning trajectory in a step-wise scan.

8. A method in accordance with claim 1, which comprises maintaining the source and detector in stationary positions while translating and rotating the object so as to effect relative movement of the source with reference to the object.

9. A method in accordance with claim 1, which comprises maintaining the object in stationary positions while moving the source and detector so as to effect relative movement of the source with reference to the object.

10. A method in accordance with claim 2 wherein the field of view is cylindrical and has a radius no greater than $r_o$ and a length no greater than $\pm A_o$, which comprises defining the scanning trajectory as $$x(\theta) = r_p \cos \theta$$

$$y(\theta) = r_p \sin \theta$$

$$z(\theta) = \begin{cases} +A_p \text{ for } 0 < \theta < \frac{\pi}{2} \text{ and } \pi < \theta < \frac{3\pi}{2} \\ -A_p \text{ for } \frac{\pi}{2} < \theta < \pi \text{ and } \frac{3\pi}{2} < \theta < 2\pi, \\ Z \text{ where } -A_p \leq Z \leq A_p \text{ for } \theta = 0, \frac{\pi}{2}, \pi, \frac{3\pi}{2} \end{cases}$$

where $r_p$ is the radius of the scanning trajectory, $A_p$ is the amplitude of the scanning trajectory; and the following conditions are met:

$$\alpha = \sqrt{2}, \text{ and } \beta = 1$$

-continued where $\alpha = \dfrac{r_p}{r_0}$ and $\beta = \dfrac{A_p}{A_0}$.

11. A method in accordance with claim 3 wherein the field of view is cylindrical and has a radius no greater than $r_o$ and a length no greater than $\pm A_o$, which comprises defining the scanning trajectory as $$x(\theta) = r_p \cos\theta$$

$$y(\theta) = r_p \sin\theta$$

$$z(\theta) = \begin{cases} +A_p \text{ for } 0 < \theta < \dfrac{\pi}{2} \text{ and } \pi < \theta < \dfrac{3\pi}{2} \\ -A_p \text{ for } \dfrac{\pi}{2} < \theta < \pi \text{ and } \dfrac{3\pi}{2} < \theta < 2\pi, \\ Z \text{ where } -A_p \leq Z \leq A_p \text{ for } \theta = 0, \dfrac{\pi}{2}, \pi, \dfrac{3\pi}{2} \end{cases}$$

where $r_p$ is the radius of the scanning trajectory, $A_p$ is the amplitude of the scanning trajectory; and the following conditions are met:

$$\alpha = \beta = 1.34$$

where $\alpha = \dfrac{r_p}{r_0}$ and $\beta = \dfrac{A_p}{A_0}$.

12. A scanning and data acquisition system for three-dimensional computerized tomography (CT) imaging of a field of view containing at least a portion of an object illuminated by a cone beam source, said system comprising:
 a cone beam source;
 a two-dimensional array detector fixed in spaced alignment with reference to said source and both the detector and the source rotatably mounted to scan the object in order to acquire cone beam projection data; and
 scanning means for effecting relative motion between said source and the object, said source moving relative to the object along a source scanning trajectory specified as a square wave on a cylindrical surface surrounding the field of view such that each plane passing through the field of view intersects the scanning trajectory in at least one point; and
 means for acquiring cone beam projection data with said source at a plurality of positions on the scanning trajectory.

13. A system in accordance with claim 12, wherein the source scanning trajectory is specified by any even number of square wave cycles on the cylindrical surface.

14. A system in accordance with claim 13, wherein the source scanning trajectory is specified by two complete square wave cycles on the cylindrical surface.

15. A system in accordance with claim 12, wherein the source scanning trajectory is specified by any odd number of square wave cycles on the cylindrical surface.

16. A method in accordance with claim 15, wherein the source scanning trajectory is specified by three complete square wave cycles on the cylindrical surface.

17. A system in accordance with claim 12, wherein said scanning means is operable to move said source relative to the object along the source scanning trajectory in a continuous scan.

18. A system in accordance with claim 12, wherein said scanning means is operable to move said source relative to the object along the scanning trajectory in a stepwise scan.

19. A system in accordance with claim 12, wherein said scanning element comprises a two-axis CNC part manipulator connected to the object for translating and rotating the object while said source and detector remain stationary.

20. A system in accordance with claim 12, wherein said scanning element comprises a two-axis CNC part manipulator connected to said source and detector for translating and rotating said source and detector about the object while the object remain stationary.

21. A system in accordance with claim 14, wherein the field of view is cylindrical and has a radius no greater than $r_o$ and a length no greater than $\pm A_o$, and wherein the scanning trajectory is defined as $$x(\theta) = r_p \cos\theta$$

$$y(\theta) = r_p \sin\theta$$

$$z(\theta) = \begin{cases} +A_p \text{ for } 0 < \theta < \dfrac{\pi}{2} \text{ and } \pi < \theta < \dfrac{3\pi}{2} \\ -A_p \text{ for } \dfrac{\pi}{2} < \theta < \pi \text{ and } \dfrac{3\pi}{2} < \theta < 2\pi, \\ Z \text{ where } -A_p \leq Z \leq A_p \text{ for } \theta = 0, \dfrac{\pi}{2}, \pi, \dfrac{3\pi}{2} \end{cases}$$

where $r_p$ is the radius of the scanning trajectory, $A_p$ is the amplitude of the scanning trajectory; and the following conditions are met:

where $\alpha = \dfrac{r_p}{r_0}$ and $\beta = \dfrac{A_p}{A_0}$.

22. A system in accordance with claim 14, wherein the field of view is cylindrical and has a radius no greater than $r_o$ and a length no greater than $\pm A_o$, and wherein the scanning trajectory is defined as $$x(\theta) = r_p \cos\theta$$

$$y(\theta) = r_p \sin\theta$$

$$z(\theta) = \begin{cases} +A_p \text{ for } 0 < \theta < \dfrac{\pi}{2} \text{ and } \pi < \theta < \dfrac{3\pi}{2} \\ -A_p \text{ for } \dfrac{\pi}{2} < \theta < \pi \text{ and } \dfrac{3\pi}{2} < \theta < 2\pi, \\ Z \text{ where } -A_p \leq Z \leq A_p \text{ for } \theta = 0, \dfrac{\pi}{2}, \pi, \dfrac{3\pi}{2} \end{cases}$$

where $r_p$ is the radius of the scanning trajectory, $A_p$ is the amplitude of the scanning trajectory; and the following conditions are met:

$$\alpha = \beta = 1.34$$

where $\alpha = \dfrac{r_p}{r_0}$ and $\beta = \dfrac{A_p}{A_0}$.

* * * * *